United States Patent
Petersvik

(10) Patent No.: US 6,705,324 B1
(45) Date of Patent: Mar. 16, 2004

(54) INCISE SYSTEM FOR SURGICAL DRAPES AND A METHOD OF USING THE SAME

(75) Inventor: Alf Petersvik, Mosjoen (NO)

(73) Assignee: Polar Medica AS, Bergen (NO)

( * ) Notice: Subject to any disclaimer, the term of this patent is extended or adjusted under 35 U.S.C. 154(b) by 0 days.

(21) Appl. No.: 09/581,705

(22) PCT Filed: Jan. 8, 1999

(86) PCT No.: PCT/NO99/00007

§ 371 (c)(1),
(2), (4) Date: Jun. 16, 2000

(87) PCT Pub. No.: WO00/25693

PCT Pub. Date: May 11, 2000

(30) Foreign Application Priority Data

Oct. 16, 1998 (NO) .......................................... 19984829

(51) Int. Cl.[7] .............................................. A61B 19/00
(52) U.S. Cl. ....................................... 128/849; 128/853
(58) Field of Search ................................. 128/849–856

(56) References Cited

U.S. PATENT DOCUMENTS

| | | | |
|---|---|---|---|
| 2,493,598 A | | 1/1950 | Rozek |
| 3,998,217 A | | 12/1976 | Trumbull et al. |
| 4,274,398 A | | 6/1981 | Scott, Jr. |
| 5,052,374 A | | 10/1991 | Alvarez-Jacinto |
| 5,593,397 A | * | 1/1997 | La Gro .................... 604/332 |
| 5,779,657 A | * | 7/1998 | Daneshvar ................. 602/79 |
| 6,032,670 A | * | 3/2000 | Miller ....................... 128/853 |

FOREIGN PATENT DOCUMENTS

| | | |
|---|---|---|
| DE | 1566069 | 12/1969 |
| EP | 0156218 | 10/1985 |
| EP | 0432728 | 6/1991 |
| SE | 148164 | 9/1950 |
| WO | 9202181 | 2/1992 |
| WO | 9905973 | 2/1999 |

* cited by examiner

*Primary Examiner*—Michael A. Brown
(74) *Attorney, Agent, or Firm*—Sherman & Shalloway

(57) ABSTRACT

Surgical equipment for use with retractors in connection with surgery, comprising an adhesive patch (32) for fastening to a patient's skin surface, a surgical sheet (30) for partly covering a patient's body, and assistance ring (18) form positioning between the lower surface of the sheet and the upper surface of the adhesive patch, having a row of upwardly protruding gripping nipples (20) for sliding through a row of holes in the sheet and through corresponding shaft holes (26) on retractors (22) thereby being fastened to assistance rings. Method for use of the surgical equipment, whereby the adhesive patch (32) is fastened to the patient's skin surface, the surgical sheet (30) being placed on top of the adhesive patch and the patient's body, the assistance ring (18) with outwardly protruding ring nipples (20) being led between the sheet's lower surface and the adhesive patch's upper surface, sliding the outwardly protruding ring nippels through the sheet's row of holes and through corresponding shaft holes (26) on the retractor (22), which thereby is fastened to the assistance ring and, after earlier outward pulling of incision edges, serves for fastening of the edges into immovable position, without participation of assistance personnel.

2 Claims, 5 Drawing Sheets

PRIOR ART

PRIOR ART

INCISE SYSTEM FOR SURGICAL DRAPES AND A METHOD OF USING THE SAME

The subject invention concerns equipment for use in surgery on patients, specifically a surgical sheet with accessories for use during operations, in particular combined with one or more retractors of the type "EASY HOLD" as described in detail in Norwegian patent application no. 973321, to which references are made, as well as a method of use of the equipment.

While preparing for, for instance abdomen surgery, it is comment to wash and sterilize the patient's skin around the field of surgery, and to cover it with sheet having an opening allowing for access to said field, so that the surgery may be performed under practically totally sterile conditions.

In connection with, for instance abdomen surgery, so called retractors are used for pulling the edges of the incision, so that the field of surgery is kept accessory and clear.

It is the aim of subject invention to produce surgical equipment of said type, and to advise a method of use of the equipment.

The surgical sheet and accessories mentioned initially, are aimed for use during surgery, when part of a patient's skin around the surgical field is covered by the sheet, and an assistance ring, attached to an adhesive patch under the sheet and device with a number of outwardly protruding nipples are connected to the above-mentioned retractors, by pushing the nipples through a row of holes around the opening in the sheet, and selected nipples are pushed through corresponding holes on the retractor's shaft, so that the retractors, after having pulled the incision edges outward to the perspective degree, are fastened and keep the edges immovable in the selected position.

The surgical sheet with assistance ring and adhesive patch are made from non conducive, impact resistant, acid- and heat resistant, plastic material, having the following properties as described in the subsequent claim.

Figure 1:
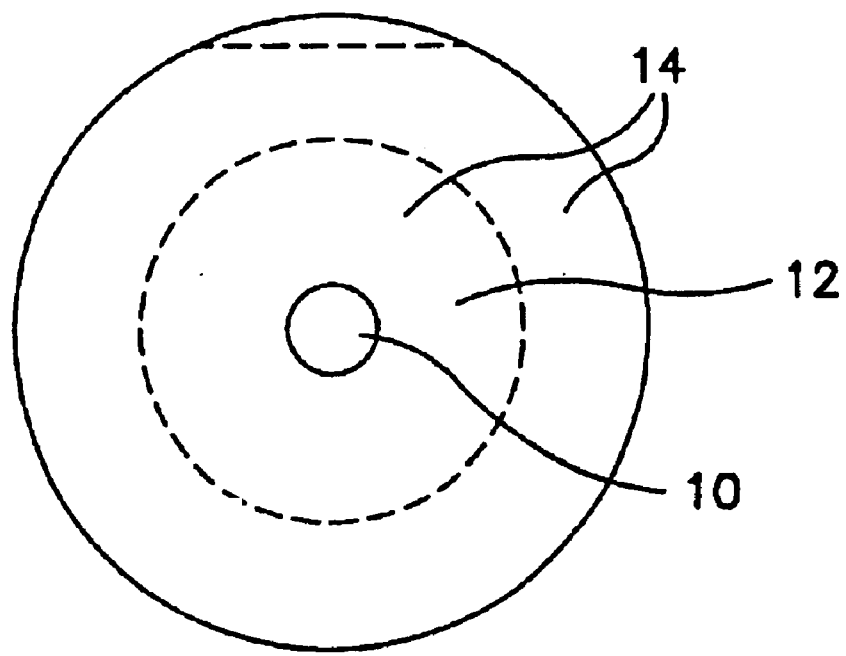

Reference is made to the attached drawing, wherein:

FIG. 1: Shows a schematic surface plan drawing of an assistance nipple described in further detail in the above-mentioned Norwegian patent application no. 973321, not included in the subject invention.

Figure 2:
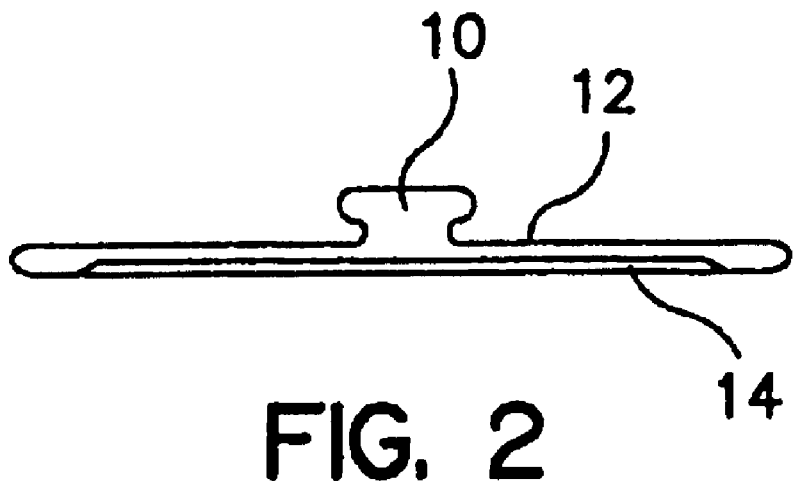

FIG. 2: Shows a schematic vertical section of the assistance nipple according to FIG. 1.

Figure 3:
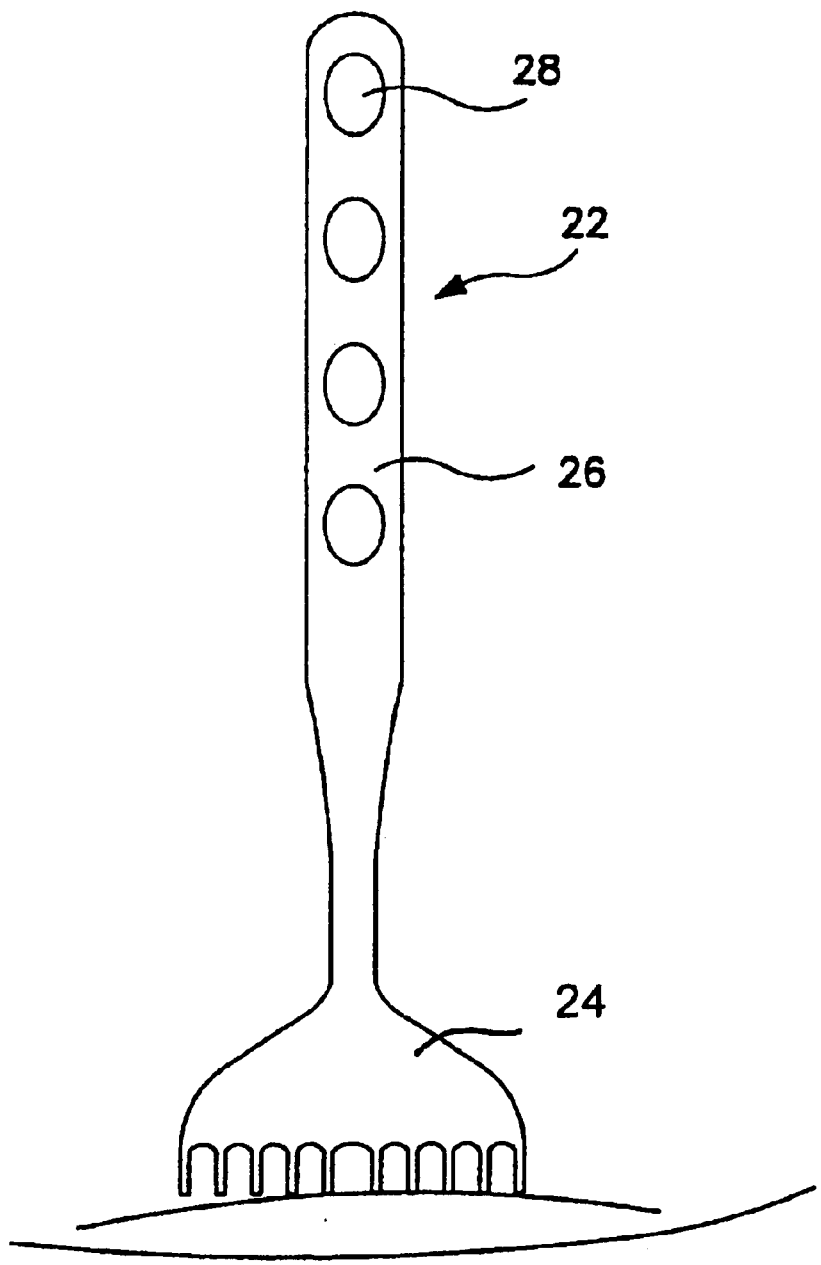

FIG. 3: Shows a schematic plan view of a retractor described in further detail in the above-mentioned Norwegian patent application no. 973321, not included in the subject invention.

Figure 4:
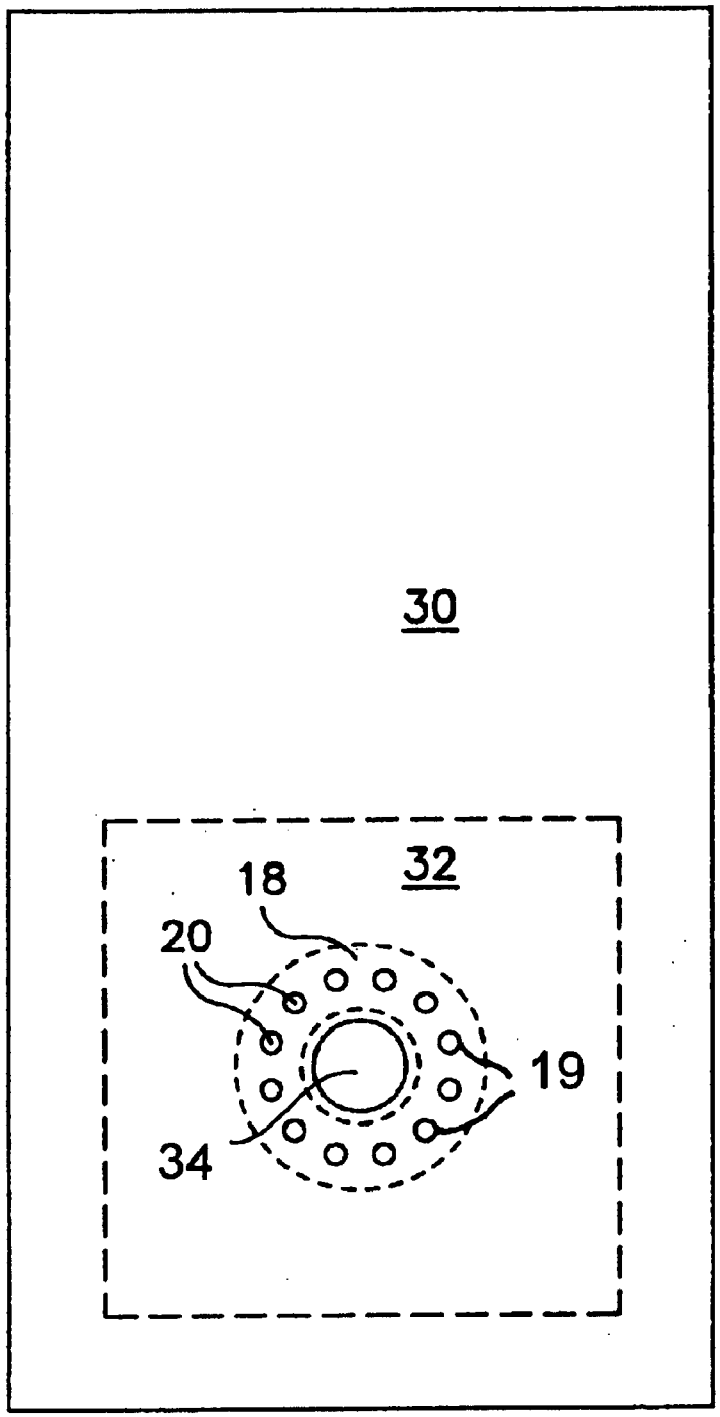

FIG. 4: Shows a schematic surface plan drawing of a surgical sheet according to the subject invention in combination with corresponding equipment in the form of an assistance ring and an adhesive patch.

Figure 5:
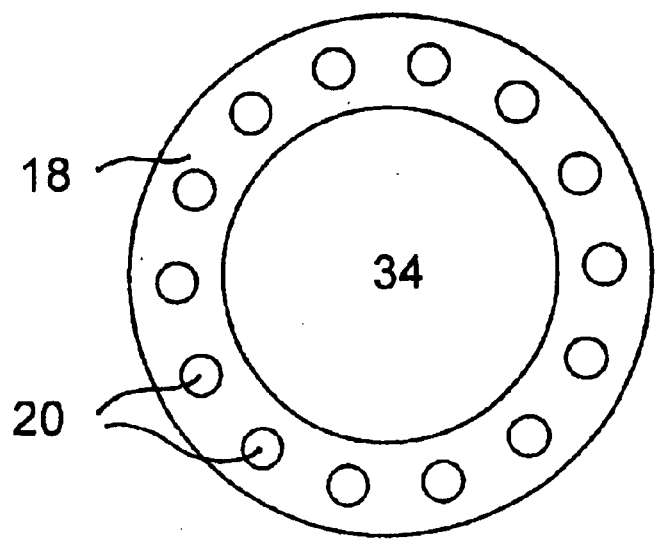

FIG. 5: Shows a schematic plan drawing of the assistance ring according to the subject invention.

Figure 6:
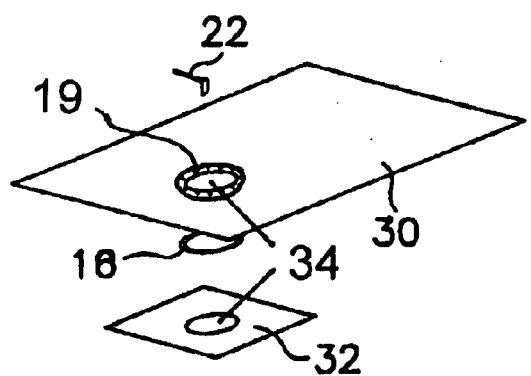

FIG. 6: Shows an expanded, schematic perspective drawing of the surgical sheet, the assistance ring and adhesive patch according to the subject invention and the retractor according to Norwegian patent application no. 973321.

In order to accommodate the understanding of the subject invention, FIGS. 1–3 indicate elements not included in the subject invention, and which are included in the previously mentioned Norwegian patent application no. 973321 "Retractor system used in surgical operations". The assistance nipple according to FIG. 1 comprises a gripping nipple 10 made in one item with a base plate 12 made from a non-conducive and impact resistant, acid and heat resistant plastic material, having an adhesive patch 14 underneath it base plate for fastening unto a patient's skin before surgery, devised for interaction with a retractor 22 (FIG. 3) for pulling out an incision edge in an operation field, and fastening of the incision edge and the retractor in position, by placing the retractor 26 onto the glued assistance nipple 10, so that the nipple is depressed and locked into one of the shaft holes 28 on the retractor 26.

The surgical equipment according to the subject invention and as shown in FIGS. 4, 5 and 6, are made from not-conducive and impact resistant, acid- and heat resistant plastic or other suitable material, comprising surgical sheet 30 with dimensions for necessary covering of part of a patient's body and during an on-going surgical incision, having a round opening 34 surrounded by a row of holes 19. The surgical equipment further includes an assistance ring 18 having a peripheral row of outwardly protruding gripping nipples 20 and an adhesive patch 32 for fastening to a patient's skin, and with a round hole 34 corresponding to the dimension of the assistance ring and the opening 34 in the plastic sheet 30.

The aim of surgical equipment described above for the subject invention, is that one or more retractors of said type may be fastened in a perspective position after pulling outwards the edge of an incision, so that the edge of the incision is maintained in immovable position without the need for assisting personnel, and that the retractor(s) if necessary may be moved and fastened in other positions by use of only one hand during surgery in process.

When starting surgery, the adhesive patch 32 is fastened onto the patient's skin in the perspective place, the sheet 30 is placed on the patient's body with the opening 34 above the adhesive patch opening 34. The assistance ring 18 is sled between the sheet's 30 underside and the upper surface of the adhesive patch 32, and with the ring's opening in line with the openings 34 of the sheet 30 and the adhesive patch 32, and with the gripping nipples 20 depressed through corresponding holes 19 around the sheet's opening 34.

After completing these preparations, and during ongoing surgery, the surgery incision's edges may be pulled outward to the degree necessary by use of one or more retractors kept in the decide position by depressing assistance ring nipples 20 through the retractor's holes 28. If one or more retractors have to be moved, this may be completed by use of only one hand, by unfastening the retractor(s) from the assistance nipple concerned, and pushing the nipple(s) through other holes (28) of the retractor's shaft, without participation of assisting personnel.

From what has been described above, will appear that the subject invention present equipment for use in connection with surgery, for instance abdomen surgery on patients. The equipment makes it possible to maintain outwardly drawn edges of surgery incisions in immovable position without time limitation, without use of assisting personnel, so that the surgery field is kept open and accessible, and the retractors may, if necessary, be unfastened and moved into other positions for refastening to assistance ring nipples by use of only one hand. Another beneficial item of the invention is that the cost of operations necessitating use of retractors and need for assisting personnel for fastening and moving of the retractors is eliminated, offering reduced costs.

What is claimed is:

1. Surgical equipment for use during surgery, for instance abdomen surgery, in particular by use of one or more interacting retractors (22), for necessary outwardly pulling and fastening into position of surgery incision, without participation of assisting personnel, for fastening or moving into other position by use of only one hand, characterized in that the equipment is made from non-conductive and impact resistant, acid- and heat resistant plastic or other suitable material, comprising an adhesive patch (32) with a round opening (34) for fastening in a desired position on a patient's body, a surgical sheet (30) for partial covering of a patient's body, and having a round opening (34) corresponding to the adhesive patch's opening and surrounded by a row of holes (19), and an assistance ring (18) between the sheet and the adhesive patch, having mainly the same inside diameter as the sheet opening and the adhesive patch's opening and equipped with a peripheral row of outwardly protruding gripping nipples (20) for entry through the row of holes (19) around the surgical sheet's opening, for depressing of chosen ring nipple(s) through corresponding shaft hole (28) on the retractor (26), aiming at fastening of the retractor(s) and fastening of outwardly drawn edges of an incision into an outwardly drawn, immovable position.

2. Method for use of the surgical equipment according to claim 1, characterized in the following steps by use of only one hand without assisting personnel, and comprising a) fastening of the adhesive patch (32) into desired position on the patient's skin, b) fastening of the assistance ring (18) onto the adhesive patch (32) with outwardly protruding ring nipples (20) and with the ring opening in line with the opening of the adhesive patch, c) placing of the surgical sheet (30) onto the assistance ring (18) and the adhesive patch (32), with the adhesive sheet's opening in line with the ring's opening and the adhesive patch's opening, d) entry of the ring nipples (20) through the row of holes (19) around the opening of the surgical sheet (34), e) outwardly pulling, to the extent desired, and fastening of the incision's edge(s) by means of retractor(s) (22), holding the surgical field open and accessible, and f) possible unfastening of the retractor(s) from the ring nipple(s), for moving and refastening into new position on the ring nipple(s).

* * * * *